United States Patent [19]
Ruskewicz et al.

[11] Patent Number: 5,377,675
[45] Date of Patent: Jan. 3, 1995

[54] METHOD AND APPARATUS FOR IMPROVED FETUS CONTACT WITH FETAL PROBE

[75] Inventors: Stephen J. Ruskewicz, Kensington; James R. Casciani, Cupertino, both of Calif.

[73] Assignee: Nellcor, Inc., Pleasanton, Calif.

[21] Appl. No.: 904,418

[22] Filed: Jun. 24, 1992

[51] Int. Cl.6 .................................................. A61B 5/00
[52] U.S. Cl. ..................................... 128/634; 128/642
[58] Field of Search ............ 128/633, 634, 664, 665, 128/642, 670, 698, 639; 604/281

[56] References Cited

U.S. PATENT DOCUMENTS

| | | | |
|---|---|---|---|
| 3,326,207 | 6/1967 | Egan | 128/642 |
| 4,813,425 | 3/1989 | Malis | 128/642 |
| 5,025,787 | 6/1991 | Sutherland et al. | 128/642 |
| 5,109,849 | 5/1992 | Goodman et al. | 128/633 |
| 5,215,090 | 6/1993 | Hon et al. | 128/642 |

*Primary Examiner*—Angela D. Sykes
*Attorney, Agent, or Firm*—Townsend and Townsend Khourie and Crew

[57] ABSTRACT

The present invention provides a method and apparatus for improved fetal contact with a fetal probe. The easily insertable probe includes a means for adjusting the position of the probe so that a sensor makes firm contact with the fetus. In one embodiment, the position is adjusted via a biasing segment of the probe which rotates about a fulcrum. In another embodiment, the position is adjusted via a bladder.

22 Claims, 6 Drawing Sheets

METHOD AND APPARATUS FOR IMPROVED FETUS CONTACT WITH FETAL PROBE

BACKGROUND OF THE INVENTION

This invention relates to fetal probes and, more particularly, to a fetal probes having improved fetal contact.

During in utero labor and delivery fetal probes are used to monitor health of the fetus. Typical parameters monitored include arterial blood oxygen saturation levels, pulse rate, heart rate and temperature. Pulse oximeters are typically used to measure various blood characteristics including arterial blood oxygen saturation and pulse rate. An electrocardiogram (ECG) is used to monitor heart rate. A thermal sensor is used to monitor temperature. In order to achieve accurate measurements, the aforementioned sensing devices must maintain good contact with the fetus during parameter measurement.

Improper contact to the fetus with a pulse oximetry probe may result in inaccuracies caused by shunting of light between the emitter and detector. FIG. 1 shows a transflectance pulse oximetry probe 110 comprising a light emitter 114 and a light detector 118 disposed within a housing 122. If the probe 110 is in poor contact with the skin 134, (e.g. due to extraneous material 138 such as hair, mucous, etc., between the probe and skin 134), light may be directly reflected from the top surface of the skin or piped through the extraneous matter as shown by path 2. Alternatively, the light may scatter below the surface of the skin, but may not travel deep enough to penetrate the blood perfused layer 130. Instead, the light travels through bloodless layer 132 as shown by path 3.

The depth uniformity and/or location of layer 132 is negatively affected by local vasoconstriction, excessive force applied to the back surface of the probe (which locally exsanguinates blood from the tissue beneath the probe), and site-to-site variations of the distance to the blood perfused layer. The aforementioned factors negatively affect blood oxygen saturation measurements. Unless probe placement is well controlled in an environment free of excessive applied force and other light shunting causes, accuracy of the calculated saturation will be suspect.

To improve contact to the fetus, the fetal probe described in pending U.S. patent application Ser. No. 07/775,315, filed Oct. 11, 1991, incorporates a fixed curved sleeve and an oppositely curved removable stiffener. The stiffener is inserted in the probe to make the handle substantially straight during insertion of the sensor housing. When the stiffener is removed, the curved sleeve presses the sensor housing against the fetus.

Similarly PCT Application No. WO 91/07910 discloses a fetal probe which has an inflatable bladder connected to the non-sensing side of the probe. The bladder has a hemispherical or spherical shape in order to provide a wedging action which will maintain the position of the fetal sensor during contractions, or fetal or maternal movements. Although the addition of an inflatable bladder improves fetal contact, unequal forces are applied to different contact points of the fetus. In addition, because of the position of the bladder, there are site-to-site variations between the sensor and the blood perfused layer. An improved method for contacting an oximeter probe to a fetus is needed.

SUMMARY OF THE INVENTION

The present invention is directed towards a method and apparatus for improved fetal contact with a fetal sensor. The present invention provides an easily insertable fetal probe which includes a means for adjusting the force to the probe sensor so that a force of sufficient magnitude is applied to prevent shunting. Proper force application increases the accuracy of measurement of the desired parameter.

In a first preferred embodiment, contact to the presenting part of the fetus is adjusted via a resilient biasing segment of the probe. The probe is a flexible elongate member having a proximal and distal end. A probe contact segment is located at the distal end of the elongate member. The probe contact segment is comprised of an active segment and a resilient biasing segment integral with the sensor body. The biasing segment changes its form during insertion of the probe to fill the space between the uterine wall and the fetus. During insertion of the probe, the biasing segment is in a deformed flattened position to make insertion into the space between the uterine wall and the fetus easier. When the probe reaches an expanded space, the biasing segment region conforms to its return position. In attempting to move to its return position, the biasing segment acts as a lever to force the probe sensor on the contact segment surface against the fetus.

In the embodiment shown in FIG. 2, a channel for stylet insertion exists along the longitudinal axis of the elongate body through the contact segment to the probe tip. Before insertion of the probe into the space between the uterine cavity and the presenting part of the fetus, a stylet is inserted into the cavity. Since the stylet is straight, the biasing segment is deformed so that the contact segment forms a straight line. Straightening the contact segment makes insertion of the probe easier. After the probe is inserted, the stylet is removed and the biased segment attempts to conform to its return position.

A third embodiment adjusts the position of the contact segment to the presenting part of the fetus through the use of an adjustable bladder. The contact segment of the oximeter probe includes a first contacting surface for sensor contact to the fetus and second face for contact to the uterine wall. An adjustable bladder is connected to the surface opposite to the sensor. In one embodiment, the adjustable bladder is filled with fluid prior to insertion. In an alternate embodiment, the bladder is inflated after insertion via an inflation tube which runs along the longitudinal axis of the probe. The bladder is generally rectangular so that each contact point along the bladder surface is equidistant to the sensing sensor contact surface. The fluid in the bladder adjusts to apply pressure to the sensor contact surface. The pressure within the bladder adjusts to prevent exsanguination.

A further understanding of the invention may be had with reference to the following description and drawings.

DETAILED DESCRIPTION OF PREFERRED EMBODIMENTS

Figure 1:
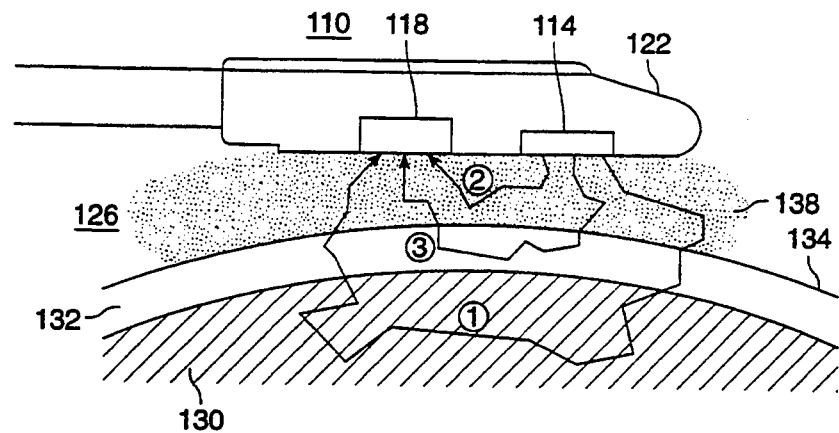
FIG. 1 is a cross-sectional diagram of a fetal probe showing light transmission through various layers of tissue.
Figure 2:
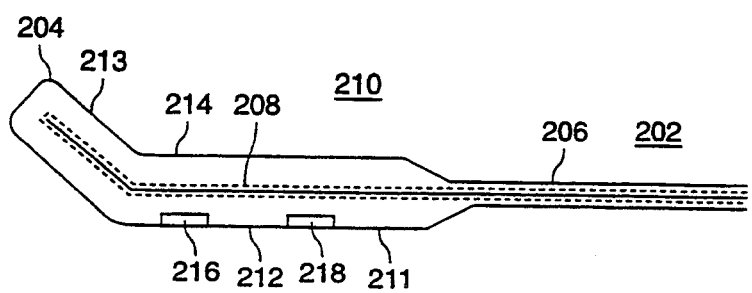
FIG. 2 is a side view of an integral end fulcrum type fetal probe according to the present invention.

FIG. 2 shows a side view of a fetal probe 200 having an integral end fulcrum in its undeformed return position. The probe has an elongate body with a proximal end 202 and a distal end 204. The probe includes a handle or insertion means 206 which functions as an insertion aid. The handle 206 is generally cylindrical having a radius of 0.1 inches and is typically 13 inches long.

The probe is formed using standard manufacturing processes. A stiffener (not shown), cables forming a bus (not shown), and a channel 208 extend along the longitudinal axis of the elongate body. The steel stiffener provides the general shape of the probe and in one embodiment terminates at the handle 206 of the probe. The stiffener allows for bending in a first direction while resisting bending in a second direction. The channel 208 is formed using standard extrusion techniques by extruding over an aluminum spacer that is removed after the formed cable is cut into individual lengths. In one embodiment, the channel 208 provides a space for stylet insertion. The cables are soldered to an electrical optical module to achieve electrical contact. This assembly is then over molded with a thermoplastic rubber by an injection molding process designed to maintain good shut-off with electrical sensing surface and optical sensing surface. A mandril is used to form a channel in sensor body for the insertion of removable stylet.

The probe extends from the insertion means at the proximal end of the probe slightly widening into the contact segment 210. The contact segment 210 is located at the distal end 204 of the probe and is comprised of an active segment 211 and resilient biasing segment 213. In the embodiment shown in FIG. 2, the active segment 211 extends from the inserting means 206 and the resilient biasing segment 213 extends from the distal end of the active segment 211. In the embodiment shown in FIG. 2, the contact segment 210 has a first fetal contact surface 212, for contact to the fetus, and second contacting surface 214 for contacting the maternal tissue. An emitter 216 and photodetector 218 are located on the first contacting surface 212 of the contact segment 210. In order to receive an accurate measurement, the emitter and photodetector 216 and 218 must be in firm contact with the fetus.

Figure 3:
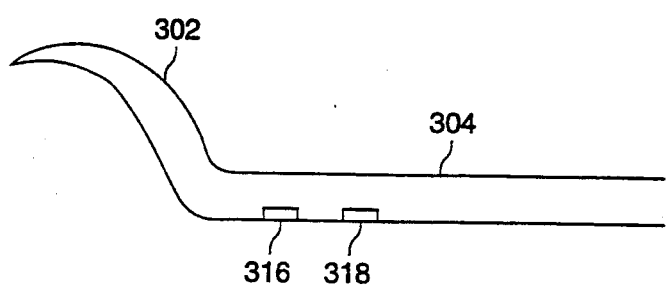
FIG. 3 is a side view of the preferred embodiment of the integral end fulcrum type fetal probe according to the present invention.

FIG. 3 is a side view of the preferred embodiment of the integral end fulcrum type fetal probe according to the preferred embodiment. The probe contact segment 302 is located at the distal end of the elongate member. Similar to the embodiment shown in FIG. 2, the probe contact segment 302 is comprised of an active segment 304 and a resilient biasing segment 306. The biasing segment 306 changes its form during insertion of the probe, expanding to fill the space between the uterine wall and the fetus. During insertion of the probe, the biasing segment 306 is deformed or preloaded to a flattened position to make insertion into the space between the uterine wall and the fetus easier. When the probe reaches an expanded space, the biasing segment adjusts to its return position. In attempting to move to its return position, the resilient biasing segment acts as a lever to force the probe sensor on the surface of the contact segment against the fetus.

The shape of the contact segment 302 shown in FIG. 3 differs from the contact segment 210 of the fetal probe shown in FIG. 2. Although both probes include a resilient biasing segment, the probe tip of the biasing segment shown in FIG. 3 is tapered to make insertion easier. Also, the deformation region 306 (in its return position) is curved in contrast to the linear biasing segment 213 shown in FIG. 2. The curvature of the biasing segment 306 is similar to the curvature of the fetus head. The curved deformation region 306 makes insertion easier.

Figure 4:
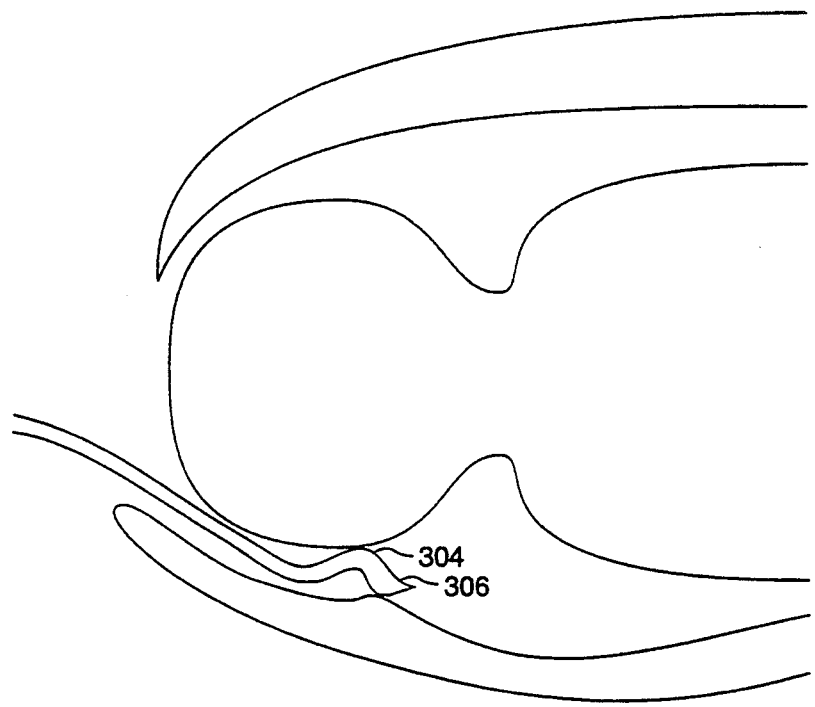
FIG. 4 is a cross-sectional view of an integral end fulcrum type fetal probe of FIG. 3 inserted in the space between the uterine cavity and the presenting part of the fetus.

FIG. 4 shows a cross-sectional view of an integral end fulcrum type fetal probe of FIG. 3 inserted in the space between the uterine cavity and the presenting part of the fetus. The fetal probe is positioned in the space between the uterine cavity and the fetus to provide good sensor contact. When the distal end is in contact with the mother's uterine wall, the region forces the emitter 316 and photodetector 318 against the fetus. To firmly contact the emitter and photodetector 318, the contact segment 302 is in its bent, undeformed position. However, although this position provides a good contact, the undeformed position makes probe insertion difficult.

Figure 5:
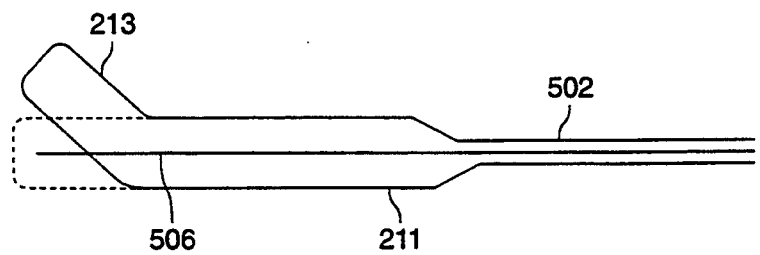
FIG. 5 is side representational view of a fulcrum type fetal probe shown in FIG. 2 in its deformed and return positions.

FIG. 5 is a side representational view of the integral end fulcrum oximeter probe shown in FIG. 2 in a first deformed and second return position. The contact segment 210 of the probe includes a fulcrum point 506 and a biasing segment 504. Since insertion of the probe is difficult with the biasing segment 504 bent towards the longitudinal axis of the handle 206, the present invention presents a second straightened position for insertion of the probe. In the first position (represented by dotted lines) the biasing segment 213 is in a position for insertion of the probe. The body of the probe is straightened for insertion by introduction of a stylet into the cavity 208 along the longitudinal axis of the probe, thereby preloading the biasing segment 504. The stylet 502 is typically a substantially flat rod made of stainless steel having a width 0.125 inches and an approximate length of 14 inches. The width of the stylet must be less than the width of the cavity 208.

When the stylet 502 is removed, the biasing segment 504 of the probe returns to its original position by rotating around its fulcrum point 506 to form an angle. The angled position of the biasing segment 213 presses the emitter and photodetector 216, 218 on the first contacting surface of the contact segment against the fetus. As the biasing segment 213 moves closer to the longitudinal axis of the probe, the emitter and photodetector 216, 218 are moved into a closer contact position with the fetus.

Although the embodiment shown in FIGS. 2 and 5 include a channel for stylet insertion, deformation of the biasing segment by a stylet is not necessary if the biasing segment is sufficiently resilient. In the embodiment shown in FIG. 3, no stylet is needed to deform the biasing segment 305.

Figure 6:
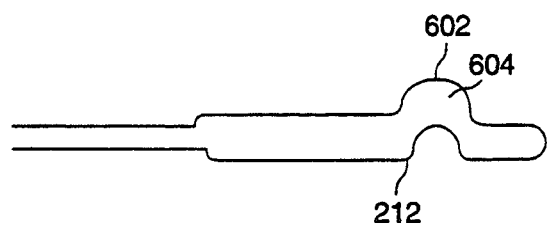
FIG. 6 shows a side representational view of a fetal probe having a corrugated contact segment.

FIG. 6 is an alternate embodiment of an integral end fulcrum fetal probe. Instead of the probe contact segment forming an angle around the fulcrum as seen in FIGS. 2, 3 and 5, the contacting segment 602 is aligned with the longitudinal axis of the handle. The contacting segment includes at least one corrugation 604 aligned to the longitudinal axis of the probe.

The dotted lines shown in FIG. 6 are representative of the probe during stylet insertion. The corrugated region 604 of the contact segment 602 is straightened during insertion of the probe into the space between the interuterine cavity and the fetus by introduction of a stylet. Moving the stylet causes the sensor to straighten (as seen in the dotted lines), thereby preloading this resilient biasing segmentor to become more "arched". This allows external control of the contact pressure between the sensor and the fetal tissue when the sensor is positioned between the fetus and the uterine wall. Removal or withdrawal of the stylet allows the sensor body to return to its normally corrugated shape. The corrugated shape conforms to gaps between the fetus and the uterine wall, firmly positioning the probe so that the sensors on the first contacting surface 212 of the probe make good contact to the fetus.

Figure 7:
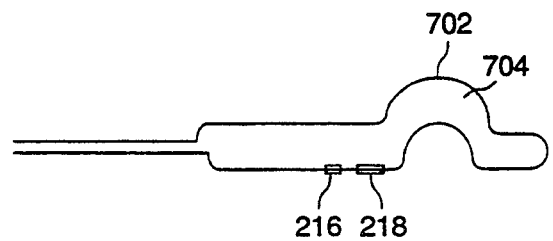
FIG. 7 shows a side view of a fetal probe having a corrugated contact segment.

To make good contact, the emitter 216 and photodetector 218 must be located on a contact surface in a region generally parallel to the surface of the fetus. In FIG. 6, the first contacting surface 212 contacts the fetus. Alternatively as shown in FIG. 7, the emitters and photodetector 216, 218 can be positioned in the region parallel to the fetus between the handle 206 and the peak 706 of the peak of the corrugation 704.

Figure 8:
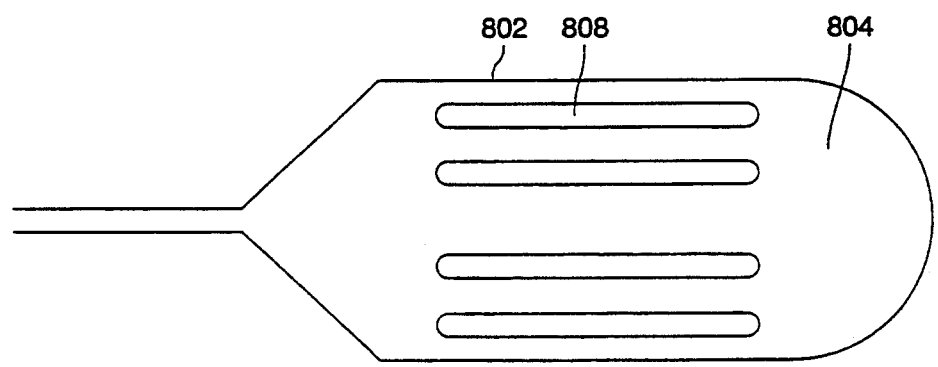
FIG. 8 is a top view of a fetal probe having collapsible runners.

FIG. 8 shows an alternate embodiment of an integral end fulcrum type oximeter probe. In the embodiment shown in FIG. 8, the contact segment 802 extends from the probe handle 804 such that the width of the contact segment 802 is wider than the handle 804. The width gradually increases to a second width which is the contact segment width. The wider body of the contact segment 802 increases the stability of the probe making it more resistant to movement within the gap between the fetus and uterine wall.

Figure 9:
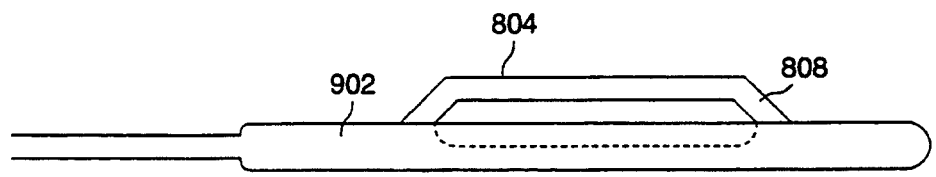
FIG. 9 is a side cross-sectional view of the fetal probe of FIG. 8 having collapsible runners.

The contact segment 802 has first contact surface 804 and a second contact surface (not shown), on the reverse side. The second contact surface 806 contacts the uterine wall and includes a plurality of runners 808 which extend substantially parallel to the longitudinal axis of the handle 804. The runners 808 are flexible elements which deflect downwards into slots inside the contact segment 802 at insertion so that insertion of the probe is not impeded. The insertion slots 902 shown in FIG. 9 allows the runners to deflect downwards below the contacting surface of the contact segment upon insertion to preload the biasing runners 808.

Figure 10:
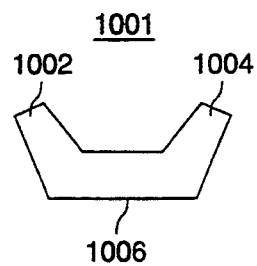
FIG. 10 is an end view of a modified fulcrum type fetal probe having flexible wings.

FIG. 10 is an end view of the contact segment 1001 fulcrum type sensor which is modified to include a first and second biasing segments fold 1002, 1004 (wings) to improve contact to the fetus. The biasing segments 1002, 1004 extend from the lateral edges of the active face 1006 of the contact segment 1001. Unlike the fulcrum type sensor shown in FIGS. 2 and 3 where the rotation occurs perpendicular to the longitudinal axis of the probe, the rotation of the first and second folds occurs along a first and second axis parallel to the longitudinal axis of the probe. In a first embodiment, the contact segment is made of a flexible rubber compound which easily deforms upon insertion of the probe into the space between the uterine wall and the presenting part of the fetus. No stylet is necessary for deformation.

In a second embodiment the biasing segment 1002, 1004 are relatively inflexible. In order to straighten the folds 1002, 1004 of the contact segment for insertion, the type of stylet used in FIG. 2 must be modified to include a first and second flexible protrusion along the sides of the stylet. The flexible protrusion are withdrawn into insertion slots during probe insertion. When the modified stylet reaches the contact segment, the modified stylet moves the stylet folds of the contact segment to a second position such that the first and second folds are at a 180° angle from each other to preload the biasing segments.

An alternate fetal probe connects an adjustable expansion means, typically a balloon, to the non-sensing side of the contact means. The adjustable expansion means is typically filled with a fluid to control the force and pressure between the sensors and the fetus and compensates for the gaps between the fetus and the uterine wall. A fluid, such as saline, is typically used.

Figure 11:
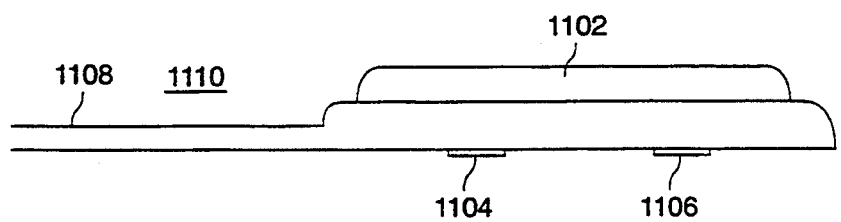
FIG. 11 is a side view of a fetal probe having a bladder type contact member according to the present invention.

FIG. 11 is a side view of a pulse oximetry probe with a bladder connected to the non-sensing side of the contact segment. The side of the probe opposite to the bladder 1102 includes an emitter 1104 and photodetector 1106. In one embodiment, a fluid transmission cavity 1108 exists within the handle means and extends from the handle means 1110 into the bladder 1102. The bladder 1102 is deflated upon insertion for ease of insertion. After insertion, fluid is transferred via the fluid transmission cavity, slowly filling the bladder 1102 until a desired pressure is reached. In a preferred embodiment, the bladder is filled with fluid and sealed before insertion into the uterus. The bladder may not be completely filled so that the fluid may move within the bladder to adjust to fill the gap between the uterus and fetus.

Figure 12:
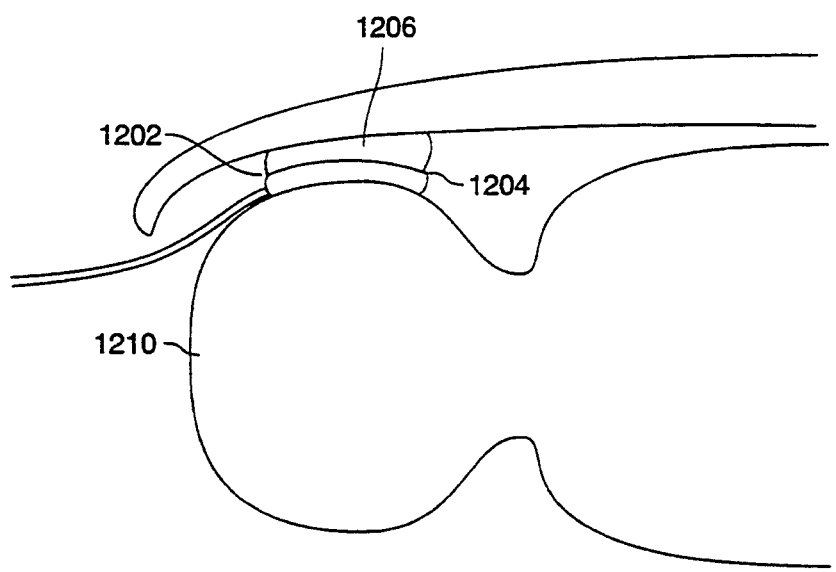
FIG. 12 is a cross-sectional view of a pulse oximetry probe with contact bladder surface inserted in the gap between the uterine wall and the fetus.

FIG. 12 is a cross-sectional view of the pulse oximetry probe with bladder of FIG. 11 inserted in the space between the uterine wall and the fetus. As can be seen from FIG. 12, the space between the uterine wall and the fetus on a first side of the probe 1202 is smaller than the space between the uterine wall and the fetus at a second side of the probe 1204. Although the space between an uterine wall and the fetus varies between the two sides 1202, 1204 of the probe, the compliant property of the fluid in the bladder 1206 and the length of the bladder allows a uniform pressure between the sensor 1208 and the fetus 1210 by movement of the fluid within the bladder to provide contact with the uterine wall along multiple points. The bladder 1206 is sufficiently long to allow the fluid to move from one part of the chamber to a more distant part, making it thin at one end and thick at the other. This allows the sensor to pass through a narrow gap. As it initially enters the gap, the distal end thins as liquid is forced back. After the distal end passes through the gap, the liquid can shift again, making the distal end thick and the proximal end passing through the gap thin. This process may be reversed with fluid being transferred from the distal end to the proximal end of the bladder.

The fluid filled bladder may be filled before insertion into the uterine gap or after insertion into the gap between the uterus and the fetus. If the bladder is filled with fluid before insertion of the probe into the gap, the volume in the bladder is non-varying. Although an equal pressure is applied to the sensors, this pressure may vary based on forces due to contraction of the uterus during labor. During a contraction, the space between the uterine wall and the fetus will decrease applying a larger force to the sensor. Thus, the pressure to the sensor is increased. Since excess force may cause local exsanguination, it may be desirable to adjust the amount of fluid in the chamber in order to apply an equal pressure at all times. This is accomplished since the length of the bladder allows the shifting of the fluid in the bladder away from any local constriction.

Figure 13:
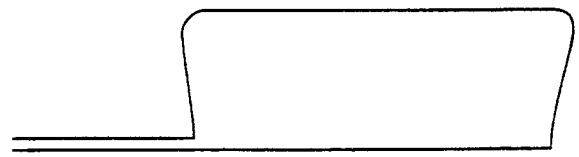
FIG. 13 is a side view of a bladder type probe oximeter where the bladder is shaped in the form of bellows.
Figure 14:
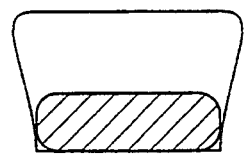
FIG. 14 is a cross-sectional view of the fetal probe shown in FIG. 15 with an inflated bladder.
Figure 15:
FIG. 15 is a cross-sectional view of the fetal probe with a bladder in a shape of bellows of FIG. 13 with a deflated bladder.

In the embodiment shown in FIG. 11, the shape of the inflatable bladder is generally rectangular so that each point of the surface of the bladder is equal distant from the sensing means. In the alternate embodiment shown in FIGS. 13–15, the shape of the adjustable expansion means is that of a bellows. When the adjustable expansion means 1302 is deflated, the bladder includes a plurality of folds parallel to the longitudinal axis of the probe handle. FIG. 13 shows a side view of a bladder type expansion means after inflation of the bladder. The bladder 1302 is generally rectangular as in the embodiment shown in FIG. 11, however, a slight widening occurs from the base of the sensor to the end of the sensor contacting the uterine surface. FIG. 14 shows an end view of the contact segment when the bladder 1402 is inflated. FIG. 15 shows an end view of the contact segment when the bladder 1502 is deflated. The deflated bellows shape is very compact, allowing easy insertion.

Figure 16:
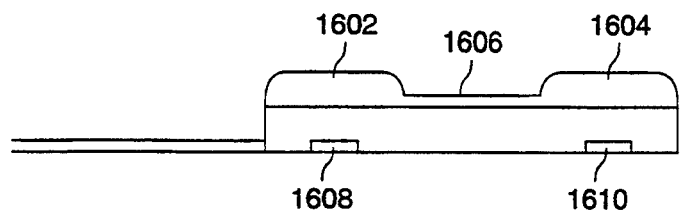
FIG. 16 is a side view of an alternate embodiment of a fetal probe having two bladders joined by a connecting passage.

In an alternate embodiment shown in FIG. 16, the expansion means consists of a first and second bladder 1602 and 1604—sufficiently separated—connected by a connecting passageway 1606. The connecting passageway 1606 between the two chambers allows the pressure to equalize within the first and second bladders. In one embodiment, the first bladder 1602 is vertically aligned with a first sensor 1608 while the second bladder 1604 is vertically aligned with a second sensor 1610 so that an equal pressure is applied directly over each sensor.

Figure 17:
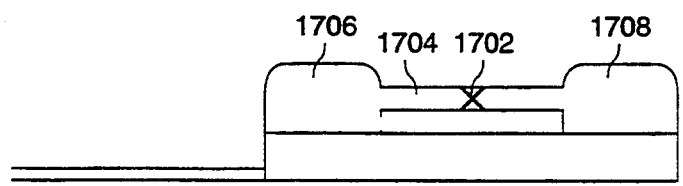
FIG. 17 is a side view of an alternate embodiment of a fetal probe having two bladders joined by a connecting passage with a restrictor in the connecting passage.

In the embodiment shown in FIG. 17, a restrictive orifice 1702 is located within the connecting passageway 1704. The restrictive orifice 1702 limits the volume of fluid which can be transmitted between the first and second bladders 1706, 1708, controlling the flow of fluid between the chambers. Restriction of the fluid flow controls the responsiveness of fluid movement to high frequency transients which occur due to changes in intrauterine pressure. This allows shifting due to prolonged changes in the gap between the fetus and the uterine wall, while avoiding noise or artifact caused by shifting of the fluid in response to short transient movements.

Figure 18:
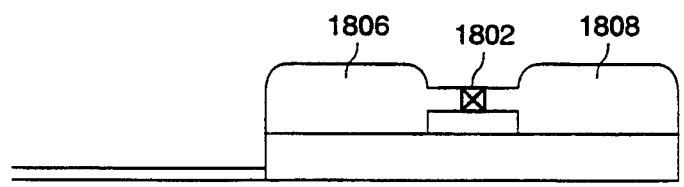
FIG. 18 is a side view of an alternate embodiment of a fetal probe having at least two inflatable bladders joined by a connecting passage with a pressure responsive valve coupled to the connecting passageway.

In the embodiment shown in FIG. 18, a pressure responsive valve 1802 is placed in the connecting passageway 1804 between the first and second bladders 1806, 1808. The pressure responsive valve may be used to equalize pressure between the two bladders. Typically the pressure responsive valve 1802 is used to equalize the pressure between the two bladders. Thus, if the pressure gets too high in the first bladder, fluid is transmitted from the first bladder to the second bladder. This improves control over transients for long-term shifts.

Figure 19:
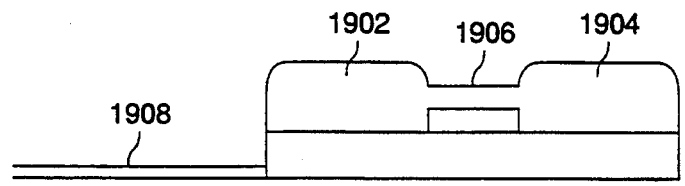
FIG. 19 is a side view of a fetal probe having a first and second bladder joined by a connecting passage wherein the fluid flow between the two bladders are controlled by an actuation means.

The embodiment shown in FIG. 19 shows two bladders 1902, 1904 connected by a connecting passageway 1906 where an actuation means 1908 is placed in the connecting passageway 1906 to control the fluid flow between the two chambers. The actuation means 1908 may be activated remotely externally to the uterus. Actuation of the device is accomplished via a connection running along the longitudinal axis of the probe. Actuation of the valve controls the movement and the direction of the flow of fluid.

The above description is illustrative and not restrictive. Many variations of the invention will become apparent to those skilled in the art on review of this disclosure. The scope of the invention should, therefore, be determined not with reference to the above description, but instead be determined with reference to the appended claims along with their full scope of equivalence.

What is claimed is:

1. An intrauterine probe for measuring a physical condition of a fetus comprising:
   a sensor body comprising an active face, wherein the sensor body has a channel disposed therein;
   inserting means for inserting the sensor body into a uterus between a fetus and a uterine wall;
   a normally deformed resilient biasing means integral with the sensor body and which is disposed entirely on the portion of the probe within the uterus for applying force between the fetus and the uterine wall; and
   straightening means for straightening the resilient biasing means, the straightening means including a stylet removably disposed in the channel.

2. The probe of claim 1 wherein the resilient biasing means extends distally from the distal end of the active face and the inserting means extends proximally from the proximal end of the active face.

3. The probe of claim 1 wherein the resilient biasing means extends distally from the distal end of the active face at an acute angle from the plane of the active face and the inserting means extends proximally from the proximal end of the active face.

4. The probe of claim 1 wherein the resilient biasing means extends from a lateral edge of the active face.

5. The probe of claim 1 wherein the resilient biasing means extends from both lateral edges of the active face.

6. The probe of claim 1 wherein the resilient biasing means comprises at least one flexible protrusion.

7. A method for measuring a physical condition of a fetus comprising the steps of:
   providing a sensor having a normally deformed resilient portion and an active face;
   inserting the sensor into a uterus such that the active face is adjacent the fetus and the resilient portion is entirely within the uterus;
   temporarily straightening the resilient portion while inserting the sensor into the uterus; and
   permitting the sensor to apply a force between the active face and the fetus using only the normal deformation of the resilient portion and without the application of any additional force from outside the uterus.

8. The method of claim 7 wherein the straightening step further comprises the step of inserting a stylet into the sensor.

9. The method of claim 8 wherein the permitting step comprises removal of the stylet from the sensor so that the resilient portion tends to return to its normally deformed state.

10. An intrauterine probe for measuring a physical condition of a fetus comprising:
    a sensor body having a longitudinal axis and an active surface for contacting a fetus;
    inserting means for inserting the sensor body into a uterus between a fetus and a uterine wall; and
    a first biasing segment extending from a rotation point on the sensor body, the first biasing segment being preformed and normally extending at a predetermined nonzero angle from the sensor body and being resilient for rotation about the rotation point.

11. The probe according to claim 10 wherein the first biasing segment terminates in a free end and functions as a lever for biasing the active surface toward the fetus when the sensor body is inserted between the fetus and the uterine wall.

12. The probe according to claim 10 further comprising straightening means for straightening the first biasing segment.

13. The probe according to claim 12 wherein the straightening means comprises means for straightening the first biasing segment.

14. The probe according to claim 13 wherein the sensor body includes a channel, and wherein the straightening means comprises a stylet removably disposed in the channel.

15. The probe according to claim 10 wherein the first biasing segment extends distally in the direction of the longitudinal axis.

16. The probe according to claim 15 wherein the first biasing segment extends distally from a distal end of the active surface, and wherein the insertion means comprises a handle extending proximally in the direction of the longitudinal axis from a proximal end of the active surface.

17. The probe according to claim 16 wherein the first biasing segment has a corrugated shape.

18. The probe according to claim 15 wherein the first biasing segment has a normally curved shape.

19. The probe according to claim 18 wherein the first biasing segment has a tapered shape.

20. The probe according to claim 10 wherein the first biasing segment extends generally perpendicularly to the longitudinal axis for rotation about the longitudinal axis.

21. The probe according to claim 20 further comprising a second biasing segment extending opposite the first biasing segment generally perpendicularly to the longitudinal axis.

22. The probe according to claim 10 wherein the sensor body has an opposite surface for facing the uterine wall, the opposite surface including a slot, and further comprising a second biasing segment connected to the first biasing segment and disposed generally parallel to the slot for deflecting into the slot when the sensor body is inserted between the fetus and the uterine wall.

* * * * *